US00PP36745P2

(12) United States Plant Patent
d'Hont et al.

(10) Patent No.: US PP36,745 P2
(45) Date of Patent: Jun. 17, 2025

(54) STRAWBERRY PLANT NAMED 'Cadenza'

(50) Latin Name: ***Fragaria* x *ananassa***
Varietal Denomination: Cadenza

(71) Applicant: FRESH FORWARD HOLDING B.V., Huissen (NL)

(72) Inventors: Rob Peter Edith d'Hont, Doorwerth (NL); Egbertus Joseph Meulenbroek, Zetten (NL)

(73) Assignee: FRESH FORWARD HOLDING B.V., Huissen (NL)

( * ) Notice: Subject to any disclaimer, the term of this patent is extended or adjusted under 35 U.S.C. 154(b) by 0 days.

(21) Appl. No.: 18/634,930

(22) Filed: Apr. 13, 2024

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208
CPC ..... A01H 5/08; A01H 5/00; A01H 6/7409; A01H 6/74
See application file for complete search history.

(56) References Cited

PUBLICATIONS

Upov Pluto 20240920 for *Fragaria* Cadenza, retrieved on Sep. 24, 2024 at https://pluto.upov.int/result, one page. (Year: 2024).*

* cited by examiner

*Primary Examiner* — June Hwu
(74) *Attorney, Agent, or Firm* — C. Anne Whealy

(57) ABSTRACT

A new and distinct cultivar of Strawberry plant named 'Cadenza', characterized by its upright plant habit; vigorous growth habit; relatively late flowering; uniform and late season fruit ripening; large conical fruits that are glossy and reddish orange in color; pleasant fruit aroma and slightly sweet/sour taste; and excellent fruit postharvest longevity.

2 Drawing Sheets

Figure 1:
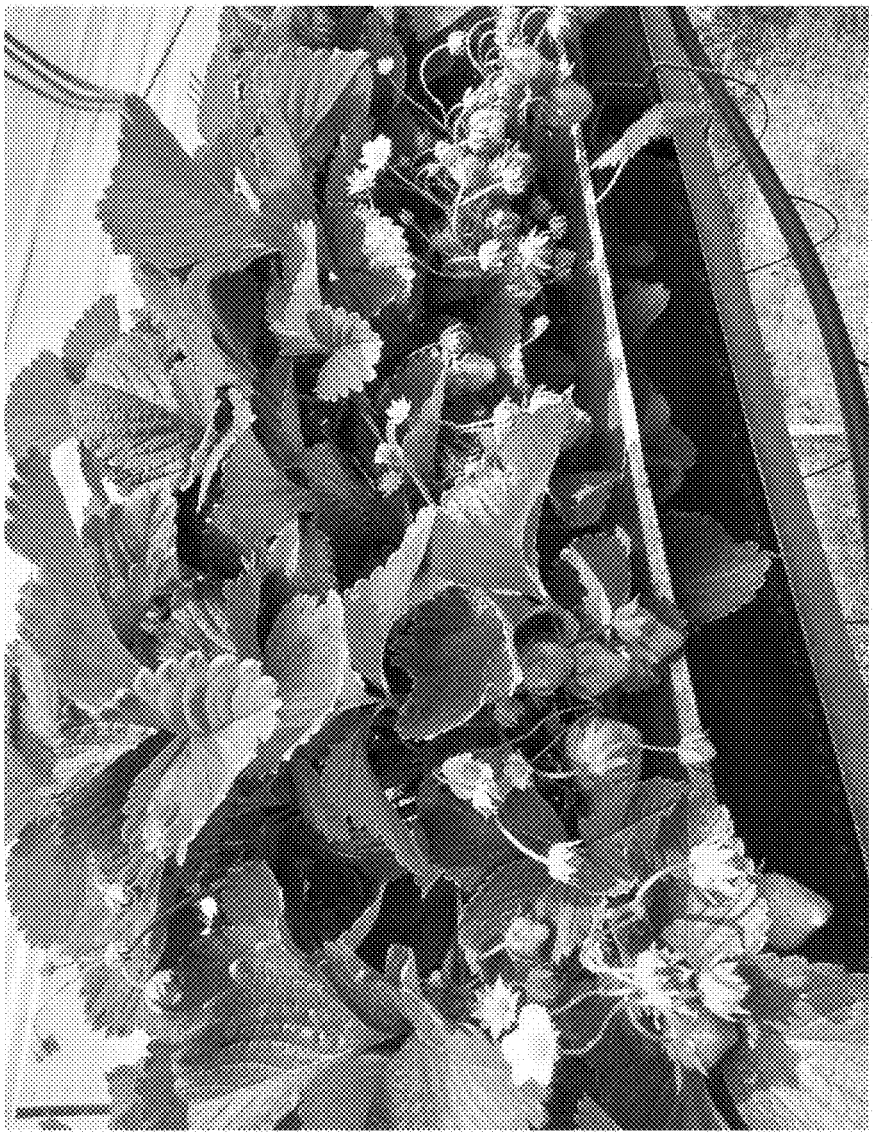

Botanical designation: *Fragaria* x *ananassa.*
Cultivar denomination: 'CADENZA'.

CROSS-REFERENCED TO CLOSELY-RELATED APPLICATIONS

Title: Strawberry Plant Named 'Ravellia'
Inventors: Rob Peter Edith d'Hont & Bert Meulenbroek
Filed: U.S. Plant Pat. No. 36,421

STATEMENT REGARDING PRIOR DISCLOSURES BY INVENTORS & APPLICANT/ASSIGNEE

A Plant Breeder's Rights application in the European Community for the instant plant was filed by the Applicant/Assignee, Fresh Forward Holding B.V. of Huissen, The Netherlands on Sep. 13, 2021, application number 2021/2253. Foreign priority is claimed to this application.

A Plant Breeder's Rights application in the United Kingdom for the instant plant was filed by the Applicant/Assignee, Fresh Forward Holding B.V. of Huissen, The Netherlands on Sep. 13, 2021, application number XU_302022000_01046. Foreign priority is claimed to this application.

A Plant Breeder's Rights application in Norway for the instant plant was filed by the Applicant/Assignee, Fresh Forward Holding B.V. of Huissen, The Netherlands on Sep. 12, 2021, application number 1766. Foreign priority is claimed to this application.

A Plant Breeder's Rights application in Switzerland for the instant plant was filed by the Applicant/Assignee, Fresh Forward Holding B.V. of Huissen, The Netherlands on Sep. 9, 2021, application number 22-3539. Foreign priority is claimed to this application.

The Inventors and Applicant/Assignee assert that no sales, offers for sale or public distribution of the instant plant occurred more than one year prior to the effective filing date of this application.

Any information about the claimed plant would have been obtained from a direct or indirect disclosure from the Inventors and/or Applicant/Assignee. Inventors and Applicant/Assignee claim a prior art exception under 35 U.S.C. 102(b)(1) for disclosures and/or sales prior to the filing date but less than one year prior to the effective filing date.

BACKGROUND OF THE INVENTION

The present Invention relates to a new and distinct cultivar of Strawberry plant, botanically known as *Fragaria* x *ananassa* and hereinafter referred to by the name 'Cadenza'.

The new Strawberry plant is a product of a planned breeding program conducted by the Inventors in Gelderland and Stevensbeek, The Netherlands. The objective of the breeding program was to develop new Strawberry plants with good fruit quality, ease of harvesting, high yield, large attractive fruits and good postharvest longevity.

The new Strawberry plant originated from a cross-pollination by the Inventors in April 2016 in Gelderland, The Netherlands of a proprietary selection of *Fragaria* x *ananassa* identified as code number E2012-1189, not patented, as the female, or seed, parent with a proprietary selection of *Fragaria* x *ananassa* identified as code number E2008-002, not patented, as the male, or pollen, parent. The new Strawberry plant was discovered and selected by the Inventors as a single plant from within the progeny of the stated cross-pollination in a controlled environment in Stevensbeek, The Netherlands in July 2018.

Asexual reproduction of the new Strawberry plant by runner cuttings in a controlled environment in Gelderland, The Netherlands since September 2018 has shown that the unique features of this new Strawberry plant are stable and reproduced true to type in successive generations of asexual reproduction.

SUMMARY OF THE INVENTION

Plants of the new Strawberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Cadenza'. These characteristics in combination distinguish 'Cadenza' as a new and distinct Strawberry plant:

1. Upright plant habit.
2. Vigorous growth habit.
3. Relatively late flowering.
4. Uniform and late season fruit ripening.
5. Large conical fruits that are glossy and reddish orange in color.
6. Pleasant fruit aroma and slightly sweet/sour taste.
7. Excellent fruit postharvest longevity.

Plants of the new Strawberry differ primarily from plants of the female parent selection in the following characteristics:

1. Leaves of plants of the new Strawberry are lighter green in color than leaves of the female parent selection.
2. Plants of the new Strawberry flower later than plants of the female parent selection.
3. Fruits of plants of the new Strawberry are conical in shape whereas fruits of plants of the female parent selection are cordate in shape.

Plants of the new Strawberry differ primarily from plants of the male parent selection in the following characteristics:

1. Plants of the new Strawberry are not as dense as plants of the male parent selection.
2. Flowers of plants of the new Strawberry are positioned at or about the foliar plane whereas flowers of plants of the male parent selection are positioned below the foliar plane.
3. Plants of the new Strawberry flower slightly earlier than plants of the male parent selection.

Plants of the new Strawberry can be compared to plants of *Fragaria* x *ananassa* 'Ravellia', disclosed in U.S. Plant Pat. No. 36,421. In side-by-side comparisons, plants of the new Strawberry differ primarily from plants of 'Ravellia' in the following characteristics:

1. Plants of the new Strawberry flower and produce fruit later than plants of 'Ravellia'.
2. Fruits of plants of the new Strawberry are orangish red in color whereas fruits of plants of 'Ravellia' are bright red in color.

Plants of the new Strawberry can be compared to plants of *Fragaria* x *ananassa* 'Vivaldi', disclosed in U.S. Plant Pat. No. 26,873. In side-by-side comparisons, plants of the new Strawberry differ primarily from plants of 'Vivaldi' in the following characteristics:

1. Plants of the new Strawberry are taller and more upright than plants of 'Vivaldi'.
2. Plants of the new Strawberry flower and produce fruit later than plants of 'Vivaldi'.
3. Fruits of plants of the new Strawberry are reddish orange in color whereas fruits of plants of 'Vivaldi' are bright red in color.

Plants of the new Strawberry can also be compared to plants of *Fragaria* x *ananassa* 'Malwina', disclosed in U.S. Plant Pat. No. 23,246. In side-by-side comparisons, plants of the new Strawberry differ primarily from plants of 'Malwina' in the following characteristics:

1. Plants of the new Strawberry are not as dense as plants of 'Malwina'.
2. Flowers of plants of the new Strawberry are positioned at or about the foliar plane whereas flowers of plants of 'Malwina' are positioned below the foliar plane.
3. Plants of the new Strawberry flower slightly earlier than plants of 'Malwina'.

BRIEF DESCRIPTION OF THE PHOTOGRAPHS

The accompanying colored photographs illustrate the overall appearance of the new Strawberry plant showing the colors as true as it is reasonably possible to obtain in colored reproductions of this type. Colors in the photographs may differ slightly from the color values cited in the detailed botanical description which accurately describe the colors of the new Strawberry plant.

The photograph on the first sheet (FIG. 1) is a side perspective view of typical flowering and fruiting plants of 'Cadenza' grown in a greenhouse environment.

Figure 2:
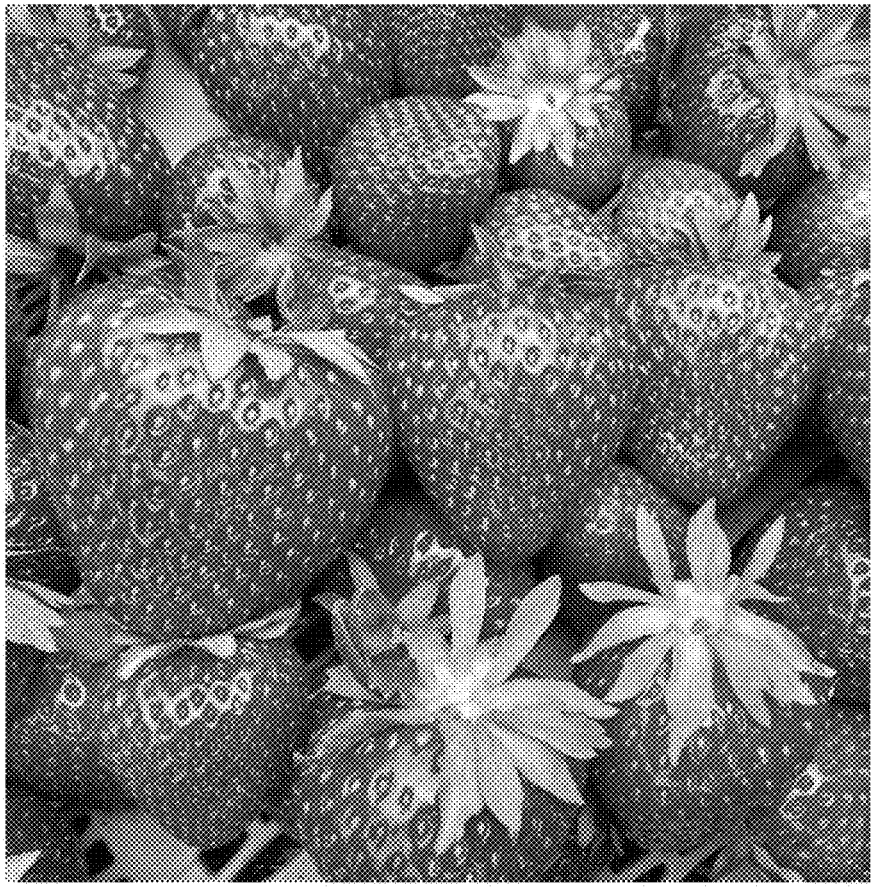

The photograph on the second sheet (FIG. 2) is a close-up view of typical developed fruits of plants of 'Cadenza'.

DETAILED BOTANICAL DESCRIPTION

The following observations and measurements describe plants grown in beds and plants grown in 4.7-liter containers with four plants per container during the winter and spring in a glass-covered greenhouse in Huissen, The Netherlands and under cultural practices typical of commercial Strawberry production. During the production of the plants, day temperatures ranged from 10° C. to 30° C. and night temperatures ranged from 8° C. to 12° C. Plants were one year old when the photographs and the description were taken. In the following description, color references are made to The Royal Horticultural Society Colour Chart, 2001 Edition, except where general terms of ordinary dictionary significance are used.

Botanical classification: *Fragaria* x *ananassa* 'Cadenza'.

Parentage:

*Female, or seed, parent.*—Proprietary selection of *Fragaria* x *ananassa* identified as code designation E2012-1189, not patented.

*Male, or pollen, parent.*—Proprietary selection of *Fragaria* x *ananassa* identified as code designation E2008-002, not patented.

Propagation:

*Type.*—By runner cuttings.

*Time to initiate roots, summer.*—About one to four days at soil temperatures about 15° C. and ambient temperatures about 17° C.

*Time to produce a rooted young plant, summer.*—About two to three weeks at soil temperatures about 15° C. to 20° C. and ambient temperatures about 17° C.

*Root description.*—Medium in thickness, fibrous; typically cream to white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Perennial; upright plant habit; leaves basal; vigorous growth habit and moderate growth rate; density of foliage, medium.

*Plant height.*—About 35 cm to 50 cm.

*Plant diameter.*—About 35 cm to 45 cm.

*Stolon quantity.*—About 10 to 15 stolons develop per plant.

*Stolon length.*—About 100 to 150 cm.

*Stolon texture.*—Sparsely pubescent.

*Stolon color.*—Close to 154D.

Leaf description:

*Arrangement and appearance.*—Basal rosette; compound with typically three leaflets per leaf; leaflets are not variegated and typically without anthocyanin when grown under normal and healthy growing conditions; if present blistering is slight.

*Leaf length.*—About 10 cm to 13 cm.

*Leaf width.*—About 9 cm to 12 cm.

*Leaflet length.*—About 6 cm to 9 cm.

*Leaflet width.*—About 4 cm to 6 cm.

*Leaflet shape.*—Broadly ovate; terminal leaflet concave in cross-section.

*Leaflet apex.*—Obtuse.

*Leaflet base.*—Attenuate.

*Leaflet margin.*—Serrate to crenate.

*Leaflet texture and luster, upper surface.*—Smooth, glabrous; moderately glossy.

*Leaflet texture and luster, lower surface.*—Pubescent; matte.

*Leaflet venation.*—Pinnate.

*Leaflet color.*—Developing leaflets, upper surface: Close to 137B. Developing leaflets, lower surface: Close to 137C. Fully expanded leaflets, upper surface: Close to 137A; venation, close to 144B. Fully expanded leaflets, lower surface: Close to 137B; venation, close to 144B.

*Petioles.*—Length: About 30 cm to 45 cm. Diameter: About 5 mm to 7 mm. Texture, upper and lower surfaces: Pubescent; hairs orientated upright. Color, upper and lower surfaces: Close to 145B.

Flower description:

*Flower form and flowering habit.*—Rotate flowers arranged singly at lateral apices; flowers held mostly upright; flowers are self-fertile; about 50 to 80 flowers develop per plant.

*Fragrance.*—None detected.

*Natural flowering season.*—Relatively late flowering habit; in the greenhouse, plants flower from mid-March to early April and in outdoor production, plants flower in May in The Netherlands.

*Flower buds.*—Length: About 1 cm. Diameter: About 1 cm. Shape: Ovoid. Aspect: Mostly upright.

*Flower diameter.*—About 2 cm to 3 cm.

*Flower depth (height).*—About 4 mm to 8 mm.

*Petals.*—Arrangement: Single whorl of five to six petals; petals imbricate. Length: About 1 cm to 1.3 cm. Width: About 1 cm to 1.3 cm. Shape: Round to broadly ovate. Apex: Rounded. Base: Obtuse. Margin: Entire. Texture, upper and lower surfaces: Smooth, glabrous; satiny. Color: When opening and fully opened, upper surface: Close to 155D; color does not change with subsequent development. When opening and fully opened, lower surface: Close to 155D; color does not change with subsequent development.

*Sepals.*—Arrangement and calyx description: Single whorl of ten to twelve sepals; calyx, star-shaped; calyx adherence is slightly inserted to level; sepals are orientated outwardly; calyx diameter is slightly smaller than developed fruit diameter. Calyx length: About 1.5 cm to 2 cm. Calyx diameter: About 2 cm to 3 cm. Length: About 1 cm to 2 cm. Width: About 3 mm to 6 mm. Shape: Lanceolate to ovate. Apex: Acute. Base: Fused. Margin: Entire. Texture, upper and lower surfaces: Pubescent. Color, upper surface: Close to 138A. Color, lower surface: Close to 137B.

*Peduncles.*—Length: About 5 cm to 20 cm. Diameter: About 1 mm to 2 mm. Strength: Strong. Texture: Pubescent; hairs orientated upright. Color: Close to between 144B and 145A.

*Reproductive organs.*—Stamens: Quantity per flower: About 25 to 30. Anther length: About 2 mm. Anther shape: Linear to elliptic. Anther color: Close to 15A. Pollen amount: Abundant. Pollen color: Close to 15B. Pistils: Quantity per flower: About 30.Pistil length: About 1 mm to 2 mm. Stigma shape: Rounded. Stigma color: Close to 5A. Fruits: Quantity per truss: About seven to ten; fruits are relatively large in size. Time to harvest: Relatively late fruit ripening, fruits; fruits are ready to harvest in late June to mid-July in The Netherlands; fruit bearing is non-remontant. Postharvest longevity: About seven to ten days at 7° C. Length: About 3 cm to 6 cm. Diameter: About 2.5 cm to 5 cm. Shape: Conical; at the apex, acute; at the base flat to rounded for primary and subsequently developing fruits, respectively. Fruit weight per fruit, first quality: About 26.6 g. Fruit weight per plant, first quality: About 1,500 g. Fruit firmness: Firm. Fragrance, taste: Pleasant; good balance between sweetness and acidity; pleasant aroma, not acidic. Total titratable acidity and sugar: About 0.56% titratable acidity and about 7.4% brix; slightly sweet/sour taste. Luster: Uniformly glossy. Surface evenness: Mostly smooth. Color, surface: Close to 40A. Color, flesh: Close to 43B and core, close to 21D. Achene quantity: Sparse to medium: about 200 to 400 per fruit. Achene position: Level with the fruit surface. Achene weight: About 0.0048 g. Achene color: Close to 1A. Band width without achenes: Not observed.

Pathogen and pest resistance: Plants of the new Strawberry have been observed to be relatively resistant to *Phytophthora cactorum, Sphaerotheca macularis* and *Verticillium dahliae*. To date, plants of the new Strawberry have not been observed to be resistant to pests and other pathogens common to Strawberry plants.

It is claimed:

1. A new and distinct Strawberry plant named 'Cadenza' as herein illustrated and described.

* * * * *